US00PP33456P2

(12) United States Plant Patent
Psenner

(10) Patent No.: US PP33,456 P2
(45) Date of Patent: Sep. 7, 2021

(54) ***TECOMA* PLANT NAMED 'TEC14004'**

(50) Latin Name: *Tecoma fulva*
Varietal Denomination: TEC14004

(71) Applicant: Spring Meadow Nursery Inc., Grand Haven, MI (US)

(72) Inventor: Thomas Psenner, Bolzano (IT)

(73) Assignee: Spring Meadow Nursery, Grand Haven, MI (US)

( * ) Notice: Subject to any disclaimer, the term of this patent is extended or adjusted under 35 U.S.C. 154(b) by 0 days.

(21) Appl. No.: 17/085,763

(22) Filed: Oct. 30, 2020

(51) Int. Cl.
*A01H 5/02* (2018.01)
*A01H 6/00* (2018.01)

(52) U.S. Cl.
USPC ..... Plt./226

(58) Field of Classification Search
USPC ..... Plt./226
See application file for complete search history.

*Primary Examiner* — Susan McCormick Ewoldt
(74) *Attorney, Agent, or Firm* — Cassandra Bright

(57) ABSTRACT

A new and distinct *Tecoma* cultivar named 'TEC14004' is disclosed, characterized by a compact growth habit and early flowering. Plants flower abundantly, produces large quantities of small flowers orange-red and yellow-orange flowers. The new variety is an *Tecoma*, normally produced as an outdoor garden or container plant.

3 Drawing Sheets

Latin name of the genus and species: *Tecoma fulva*.
Variety denomination: 'TEC14004'.

BACKGROUND OF THE INVENTION

The new *Tecoma* cultivar is a product of a controlled breeding program. The objective of the breeding program was to produce new *Tecoma* varieties with a compact plant habit and early flowering for ornamental commercial applications. The cross resulting in this new variety was made in March of 2013. The seed parent is an unpatented, proprietary variety of *Tecoma fulva* referred to as 'TEC12021'. The pollen parent is an unnamed, unpatented variety of *Tecoma fulva*. The selection of this new variety was made at a nursery in Bolzano, Italy during September of 2014.

Asexual reproduction of the new cultivar 'TEC14004' was first performed in November of 2014 at a nursery in Bolzano, Italy. Vegetative terminal cuttings were used. Subsequent propagation has shown that the unique features of this cultivar are stable and reproduced true to type in successive generations.

Date of first publication Nov. 1, 2019, occurring in Italy. This publication was made directly by the inventor, on his company's website. This disclosure falls within the exception allowed under 102(b)(1).

SUMMARY OF THE INVENTION

The cultivar 'TEC14004' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'TEC14004' These characteristics in combination distinguish 'TEC14004' as a new and distinct *Tecoma* cultivar:

1. Compact growth habit.
2. Early flowering.

3. More flowers than known varieties.
4. Smaller flowers than known varieties.

PARENT COMPARISON

Plants of the new cultivar 'TEC14004' are similar to plants of the seed parent variety in most horticultural characteristics, however, plants of the new cultivar 'TEC14004' differ in the following;

1. The new variety has a compact growth habit; the seed parent has a medium/moderate growth habit.
2. Flowers of the new variety are smaller than flowers of the seed parent.
3. Plants of the new variety begin flowering earlier than plants of the seed parent.

Plants of the new cultivar 'TEC14004' are similar to plants of the pollen parent variety in most horticultural characteristics, however, plants of the new cultivar 'TEC14004' differ in the following;

1. The new variety produces orange flowers, flowers of the pollen parent are red.
2. Flowers of the new variety are larger than flowers of the pollen parent.
3. Plants of the new variety begin flowering earlier than plants of the pollen parent.

COMMERCIAL COMPARISON

Plants of the new cultivar 'TEC14004' can be compared to the variety *Tecoma* 'Orange Jubilee', unpatented. These varieties are similar in most horticultural characteristics however, 'TEC14004' differs in the following:

1. Plants of the new variety are smaller and more compact than plants of this comparator.
2. Petals of the new variety have an undulating margin not found on flowers of this comparator.

BRIEF DESCRIPTION OF THE PHOTOGRAPHS

The accompanying photograph in FIG. 1 illustrates in full color a plant of 'TEC14004' during the Summer grown outdoors, at approximately 2 years old in a 2 gallon pot.

Figure 1:
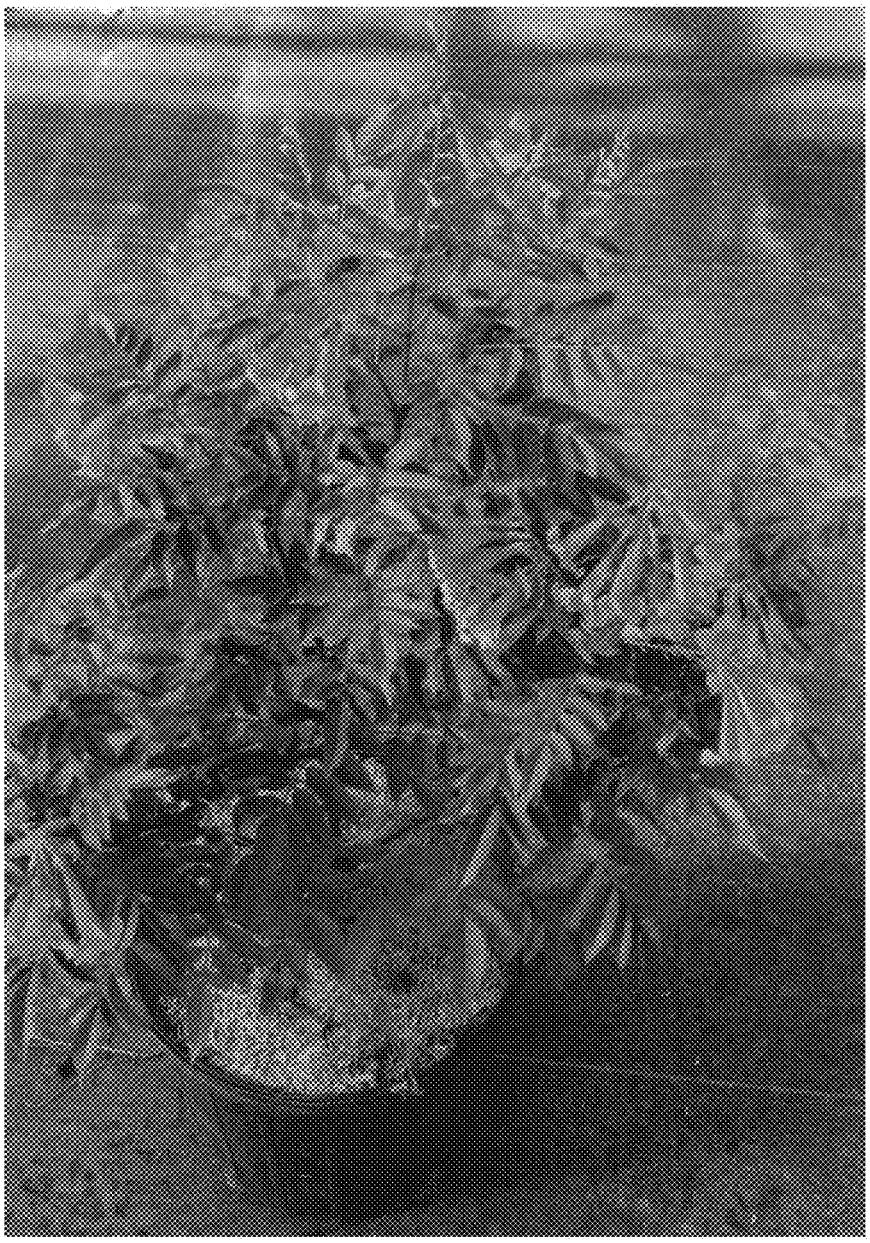
Figure 2:
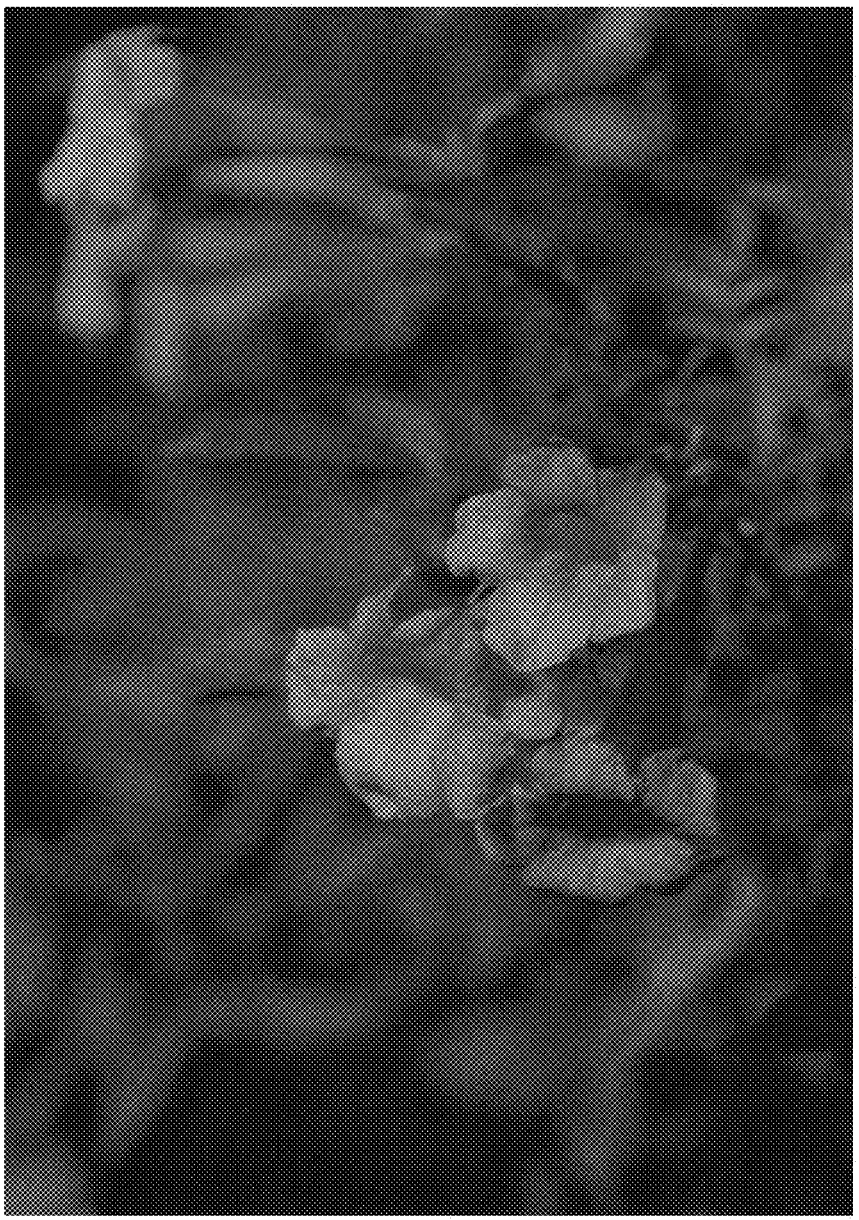
FIG. 2, illustrates a close up view of flowers of 'TEC14004'.
Figure 3:
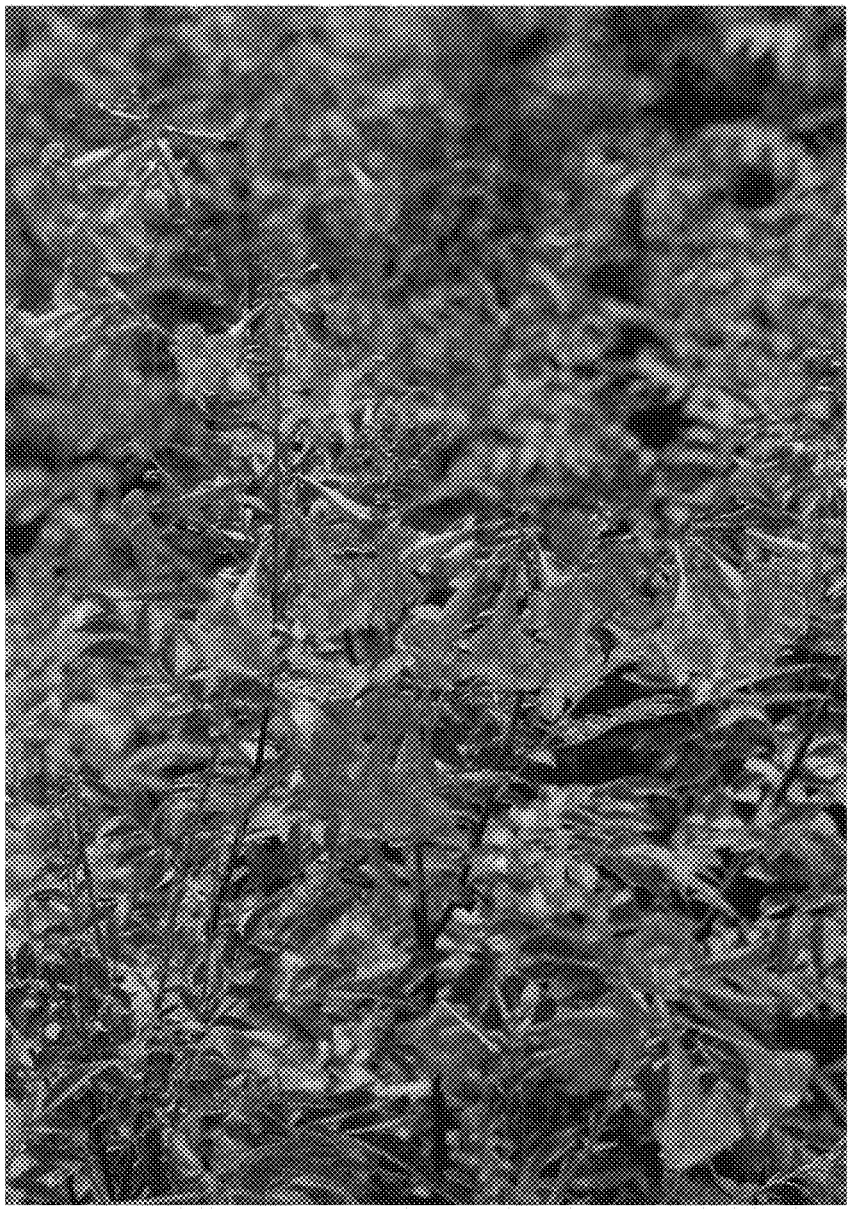
FIG. 3 illustrates flowering during late Summer.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, 6$^{th}$ edition, except where general terms of ordinary dictionary significance are used. The following observations and measurements describe 'TEC14004' plants grown in a polyhouse in Grand Haven, Mich. Measurements were taken during Summer. The plants were about 2.5 years old in 3-gallon containers. The growing temperature ranged from approximately 18° C. to 27° C. during the day and 5° C. to 10° C. at night. Measurements and numerical values represent averages of typical plant types.

Botanical classification: *Tecoma fulva* 'TEC14004'.

PROPAGATION

Time to initiate roots: About 35 days at approximately 18 to 27° C.

Time to produce a rooted young plant: About 8 weeks at approximately 18 to 27° C.

PLANT

Plant type: Perennial flowering shrub.

Age of plant described: Approximately 1.5 years old.

Growth habit: Upright, somewhat outwardly spreading.

Pot size of plant described: 3-gallon pot.

Height: 58 cm.

Plant spread: 83 cm.

Plant vigor: Moderate.

Branching characteristics: Lateral branching. Pinching required.

Length of primary lateral branches: Average 50 cm.

Diameter of lateral branches: 4 mm.

Quantity of lateral branches: Average 10.

Stem:

- *Stem shape*.—Round.
- *Stem strength*.—Strong.
- *Color*.—Near Yellow-Green 144B, oldest branches Grey-Brown 199A with striations 199D.
- *Texture*.—Rough, scaly with age.
- *Angle of attachment*.—15 to 30 degrees from center of plant.

Internode length: 4.5 cm on average.

Root description: Moderately dense, free branching, fibrous. White in color, not effectively measured with a color chart.

FOLIAGE

Leaf:

- *Arrangement*.—Opposite. Compound. Length: Average 16 cm. Width: Average 7 cm. Leaflets per leaf: 11. Rachis length: Average range 7 to 10 cm. Rachis color: Near RHS Green 143C.
- *Leaflets*.—Length: Average 5 cm. Width: Average 2 cm. Shape of blade: Elliptic. Apex: Acute. Base: Oblique. Attachment: Stalked. Margin: Serrate. Leaflet Petiole:5 mm long, 1 mm wide, colored near Green 143A. Texture of both surfaces: Glabrous, matte.
- *Color*.—Young foliage upper side: Near RHS Yellow-Green 144B. Young foliage under side: Near RHS Yellow-Green 144B. Mature foliage upper side: Near RHS Green N137B. Mature foliage under side: Near RHS Green NN 137D.
- *Venation*.—Pattern: Pinnate. Color upper side: Near RHS Yellow-Green N144D. Color under side: Near RHS Yellow-Green 144D.
- *Petiole*.—Average Length: 3 to 4 cm. Diameter: 3 to 5 mm. Petiole color upper side: Near RHS Green 143A. Petiole color lower side: Near RHS Yellow-Green 144D. Petiole Texture upper side: Smooth. Petiole Texture lower side: Smooth.

FLOWER

Natural flowering season: Summer.

Flowering form: Single funnelform flowers in terminal clusters.

Inflorescence:

- *Height*.—About 8 cm.
- *Width*.—About 11 cm.
- *Quantity of flowers*.—Average 20.

Flower:

- *Shape*.—Trumpet.
- *Length*.—5 cm.
- *Diameter*.—3.5 cm.
- *Throat diameter*.—1 cm.
- *Throat/tube length*.—4 cm.
- *Tube base diameter*.—3 mm.
- *Aspect*.—Outward and somewhat downward.
- *Persistence*.—Self-cleaning.
- *Fragrance*.—Not observed.

Bud:

- *Shape*.—Obovoid.
- *Length*.—4.5 cm.
- *Diameter*.—1 cm.
- *Color*.—Near RHS Orange-red 34B, Orange-red N34A and Yellow-Orange 21A.

Petal:

- *Petal arrangement*.—Single funnelform, separating into individual petals at tube end.
- *Number of petals per flower*.—5.
- *Petal shape*.—Ovate.
- *Petal base*.—Fused.
- *Margin*.—Undulate.
- *Tip shape*.—Obtuse.
- *Unfused length*.—13 mm.
- *Unfused width*.—15 mm.
- *Texture*.—Inner: Smooth. Outer: Smooth.

Color:

- *When opening*.—Inner surface: Mix of Orange-red 34B, Orange-red N34A and Yellow-Orange 21A. Outer surface: Mix of Orange-red 34B, Orange-red N34A and Yellow-Orange 21A.
- *Fully opened*.—Inner surface: Mix of Orange-red 34B, Orange-red N34A and Yellow-Orange 21A. Outer surface: Mix of Orange-red 34B, Orange-red N34A and Yellow-Orange 21A.

Tube color: Interior near Yellow-Orange 21A stripes Orange-Red N34A and 34B. Exterior near Orange-Red N34A and 34B with stripes Yellow-Orange 21A.

Sepal:

*Arrangement*.—Whorl.
*Number*.—Average 5.
*Shape*.—Deltate.
*Tip*.—Acute.
*Base*.—Fused.
*Margin*.—Entire.
*Length*.—2 mm.
*Width*.—1 mm.
*Texture, upper*.—Glabrous.
*Texture, lower*.—Glabrous.
*Color*.—Mature: Inner surface: Near Yellow-Green 145A. Outer surface: Near Yellow-Green 145A.

Peduncle:

*Length*.—6.5 cm.
*Diameter*.—2 mm.
*Color*.—Near Green 143A.
*Orientation*.—About 45°.
*Strength*.—Good.
*Texture*.—Smooth.

Pedicel:

*Length*.—8 mm.
*Diameter*.—1 mm.
*Color*.—Near Yellow-Green 144B.
*Orientation*.—About 90°.
*Strength*.—Good.
*Texture*.—Smooth.

REPRODUCTIVE ORGANS

Stamens:

*Number*.—Average 5.
*Filament length*.—3.0 cm.
*Filament color*.—Near RHS Greyed-Yellow 162C.

Anthers:

*Shape*.—Bi-lobed.
*Length*.—2 mm.
*Color*.—Near RHS Greyed-Yellow 162C.
*Pollen color*.—Near RHS Greyed-Yellow 162C.
*Pollen amount*.—Scant.

Pistil:

*Number*.—1.
*Length*.—3.0 cm.
*Style*.—Length: 2.0 cm. Color: Near Yellow-Green 154B.
*Stigma*.—Shape: Paddle-shaped. Color: Near Yellow-Green 154B.
*Ovary color*.—Near Yellow-Green 154B.

OTHER CHARACTERISTICS

Seeds and fruits: Not observed.

Disease/pest resistance: Neither resistance nor susceptibility to normal diseases and pests of *Tecoma fulva* have been observed.

Temperature tolerance: Typical range USDA zones 7 through 11.

What is claimed is:

1. A new and distinct cultivar of *Tecoma* plant named 'TEC14004' as herein illustrated and described.

* * * * *